(12) United States Patent
Van Hee et al.

(10) Patent No.: US 7,945,324 B2
(45) Date of Patent: May 17, 2011

(54) PRESSURE SENSING LEAD SYSTEMS FOR IMPLANTABLE STIMULATORS

(75) Inventors: Justin R. Van Hee, Minneapolis, MN (US); Andres Belalcazar, St. Paul, MN (US)

(73) Assignee: Data Sciences International, Inc., St. Paul, MN (US)

(*) Notice: Subject to any disclaimer, the term of this patent is extended or adjusted under 35 U.S.C. 154(b) by 499 days.

(21) Appl. No.: 12/165,557

(22) Filed: Jun. 30, 2008

(65) Prior Publication Data

US 2009/0326598 A1  Dec. 31, 2009

(51) Int. Cl.
*A61N 1/39* (2006.01)

(52) U.S. Cl. ............. 607/6; 607/122; 607/23; 600/485; 600/488

(58) Field of Classification Search .......... 607/6
See application file for complete search history.

(56) References Cited

U.S. PATENT DOCUMENTS

| | | |
|---|---|---|
| 3,942,536 A | 3/1976 | Mirowski et al. |
| 5,083,563 A | 1/1992 | Collins |
| 5,085,213 A | 2/1992 | Cohen |
| 5,105,810 A | 4/1992 | Collins et al. |
| 5,163,429 A | 11/1992 | Cohen |
| 5,184,614 A | 2/1993 | Collins et al. |
| 5,353,800 A | 10/1994 | Pohndorf et al. |
| 5,535,752 A | 7/1996 | Halperin et al. |
| 5,564,434 A | 10/1996 | Halperin et al. |
| 5,702,428 A | 12/1997 | Tippey et al. |
| 5,899,927 A * | 5/1999 | Ecker et al. ............ 607/23 |
| 5,904,708 A | 5/1999 | Goedeke |
| 6,144,866 A | 11/2000 | Miesel et al. |
| 6,208,900 B1 | 3/2001 | Ecker et al. |
| 6,223,081 B1 | 4/2001 | Kerver |
| 6,409,674 B1 | 6/2002 | Brockway et al. |
| 6,508,771 B1 | 1/2003 | Padmanabhan et al. |
| 6,659,595 B2 | 12/2003 | Yamaguchi et al. |
| 6,865,419 B2 | 3/2005 | Mulligan et al. |
| 7,025,727 B2 | 4/2006 | Brockway et al. |
| 7,347,822 B2 | 3/2008 | Brockway et al. |
| 7,481,774 B2 * | 1/2009 | Brockway et al. ........... 600/561 |
| 7,529,583 B1 * | 5/2009 | Brockway et al. ............ 607/6 |
| 2002/0045921 A1 | 4/2002 | Wolinsky et al. |
| 2002/0151938 A1 | 10/2002 | Corbucci |
| 2003/0023273 A1 | 1/2003 | DeGroot et al. |
| 2003/0088303 A1 | 5/2003 | Goode |
| 2004/0147993 A1 | 7/2004 | Westlund et al. |
| 2004/0167416 A1 | 8/2004 | Lee |
| 2004/0220629 A1 | 11/2004 | Kamath et al. |
| 2005/0154421 A1 | 7/2005 | Ousdigian |
| 2005/0160823 A1 | 7/2005 | Zdeblick et al. |
| 2005/0245979 A1 | 11/2005 | Belk |
| 2005/0245980 A1 | 11/2005 | Belk |
| 2005/0251217 A1 | 11/2005 | Brown |
| 2005/0288725 A1 | 12/2005 | Hettrick et al. |
| 2006/0041281 A1 | 2/2006 | Von Arx et al. |

(Continued)

*Primary Examiner* — Kennedy J Schaetzle (74) *Attorney, Agent, or Firm* — Fish & Richardson P.C.

(57) ABSTRACT

Various different implementations of lead systems are disclosed for use with implantable stimulation systems. Generally, the lead systems incorporate, within an elongate lead body, one or more electrical conduits that connect to one or more distal electrodes, and a liquid-filled pressure transmission catheter lumen that extends proximally from a distal entry port. Use of the lead systems allows accurate pressure sensing at a location near where the electrodes are positioned. In addition, a defibrillator lead is disclosed having such features, and a system using that lead is capable of directly monitoring pressure within a heart chamber, and using that information to confirm the delivery of a defibrillation pulse.

9 Claims, 7 Drawing Sheets

U.S. PATENT DOCUMENTS

| | | |
|---|---|---|
| 2006/0064135 A1 | 3/2006 | Brockway |
| 2006/0064966 A1 | 3/2006 | Opris |
| 2006/0094966 A1 | 5/2006 | Brockway et al. |
| 2006/0116593 A1 | 6/2006 | Zhang et al. |
| 2007/0027489 A1 | 2/2007 | Gill et al. |
| 2007/0118039 A1 | 5/2007 | Bodecker et al. |
| 2007/0123965 A1 | 5/2007 | Westlund et al. |
| 2007/0156189 A1 | 7/2007 | DeGroot et al. |
| 2007/0163353 A1 | 7/2007 | Lec et al. |

* cited by examiner

PRESSURE SENSING LEAD SYSTEMS FOR IMPLANTABLE STIMULATORS

TECHNICAL FIELD

This document describes implantable cardiac stimulators that use a dual-purpose lead system that senses pressure and provides connection to electrodes.

BACKGROUND

Implantable stimulators such as cardiac and nerve stimulators typically include a pulse generator component and a lead system that is connectable to the pulse generator component. The lead system may include one or more lead wires that plug in to the pulse generator component, and have one or more electrodes provided at a distal portion of the lead. Such implantable stimulators may provide stimulation to cardiac or other tissue such as nerves, as needed. In the case of cardiac stimulation, therapy may be provided in the form of pacing, cardioversion, and defibrillation pulses.

Various forms of pressure sensors are available for monitoring pressure within a living being. In addition, in the case of implantable defibrillators, it has long been believed that one way to assess whether or not to deliver a defibrillation pulse is to monitor an intracardiac pressure signal (that is, a pressure signal measured from within a chamber of the heart, such as inside the ventricle). It has proven challenging, however, to provide a viable cardiac stimulation system that enables accurate monitoring of intracardiac pressure signals, while also providing for the sensing and stimulation electrodes that are necessary in such a system. Commercial implantable defibrillator systems, for example, uniformly assess cardiac electrical information in determining if and when a defibrillation pulse should be delivered to a patient, as opposed to measuring intracardiac pressure. One reason this may be the case is that the same electrodes used for delivery of stimulation pulses are used for sensing.

Implantable stimulators may benefit from further information to analyze to determine, or confirm, that a patient is indeed in a dangerous state where a painful electrical pulse should be delivered. For example, unnecessary shocks are problematic in implantable defibrillator systems, because the shocks may be very painful to the patient.

SUMMARY

In one general aspect, there is provided various different implementations of lead systems for use with implantable stimulation systems. Generally, the lead systems incorporate, within an elongate lead body, one or more electrical conduits that connect to one or more distal electrodes, and a liquid-filled pressure transmission catheter lumen that extends proximally from a distal entry port. Use of the lead systems allows accurate pressure sensing at a location near where the electrodes are positioned.

In another aspect, an implantable defibrillator system is provided. The system includes an implantable pulse generator component and an endocardial lead. The pulse generator component is adapted for subcutaneous implantation in a subject. The endocardial lead includes an elongate lead body having a distal portion adapted for implantation within a heart chamber and a proximal portion adapted to be connected to the implantable pulse generator component, the elongate lead body having a length that extends from a chamber of a subject's heart to a subcutaneous region of the subject; an is elongate electrical conductor extending, within the lead body, from the lead body distal portion and to the lead body proximal portion; and a pressure transmission catheter comprising a lumen extending, within the lead body, from a distal pressure sensing portion positioned at the lead body distal portion and to the lead body proximal portion, the pressure transmission catheter lumen being filled with a pressure transmitting substance. The implantable pulse generator component is adapted to monitor, using the pressure transmission catheter, a pressure signal present at the distal pressure sensing portion, is adapted to evaluate the monitored the pressure signal, and is adapted to avoid application of an unnecessary defibrillating shock if the monitored pressure signal is pulsating in a manner that indicates an absence of a ventricular fibrillation condition.

In various implementations of the system, one or more of the following features may be included. The endocardial lead may include a pressure transducer positioned within the lead body proximal portion, or alternatively, the implantable pulse generator component may include a pressure transducer. The pressure transmitting substance may be a pressure transmitting liquid.

In yet another aspect, an endocardial defibrillator lead is provided. The lead includes an elongate lead body having a distal portion adapted for implantation within a heart chamber and a proximal portion adapted to be connected to an implantable pulse generator component. The elongate lead body has a length that extends from a chamber of a subject's heart to a subcutaneous region of the subject. The lead also includes an elongate electrical conductor extending, within the lead body, from a defibrillation electrode positioned at the lead body distal portion and to the lead body proximal portion. The lead also includes a pressure transmission catheter comprising a lumen extending, within the lead body, from a distal pressure sensing portion positioned at the lead body distal portion and to the lead body proximal portion, the pressure transmission catheter lumen being filled with a pressure transmitting substance.

In various implementations of the lead, one or more of the following features may be included. The lead may also include a pressure transducer positioned within the lead body proximal portion. The pressure transmission catheter of the lead may also include a piston component that moves longitudinally within the lead body in response to changes in pressure at the distal pressure sensing portion. In such a case, the piston may be adapted for attachment to, and for movement with, a component within the implantable pulse generator, so that pressure transmitted through the substance within the pressure transmission catheter lumen is detectable within the implantable pulse generator component.

In another implementation of the defibrillator lead, a proximal lead tip of the lead may be configured to mate with a lead tip receiver formed within an implantable pulse generator, and upon connection form a non-interrupted path of pressure transmitting substance that extends from the lead pressure transmission catheter lumen to a receiver pressure transmission catheter lumen provided in the implantable pulse generator. The pressure transmitting substance may be a pressure transmitting liquid.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Generally, this document describes implantable electrical stimulation systems that use dual-purpose lead systems that both provide electrical connection to distal electrodes (for sensing electrical activity and/or delivering stimulation pulses), and provide an internal liquid-filled pressure transmission catheter (PTC) lumen for transmitting a distally sensed pressure signal proximally to a proximal pressure transducer. Systems employing such a dual-purpose lead system provide the addition of an accurate way of measuring pressure at a location near where the system's electrodes are positioned.

Figure 1:
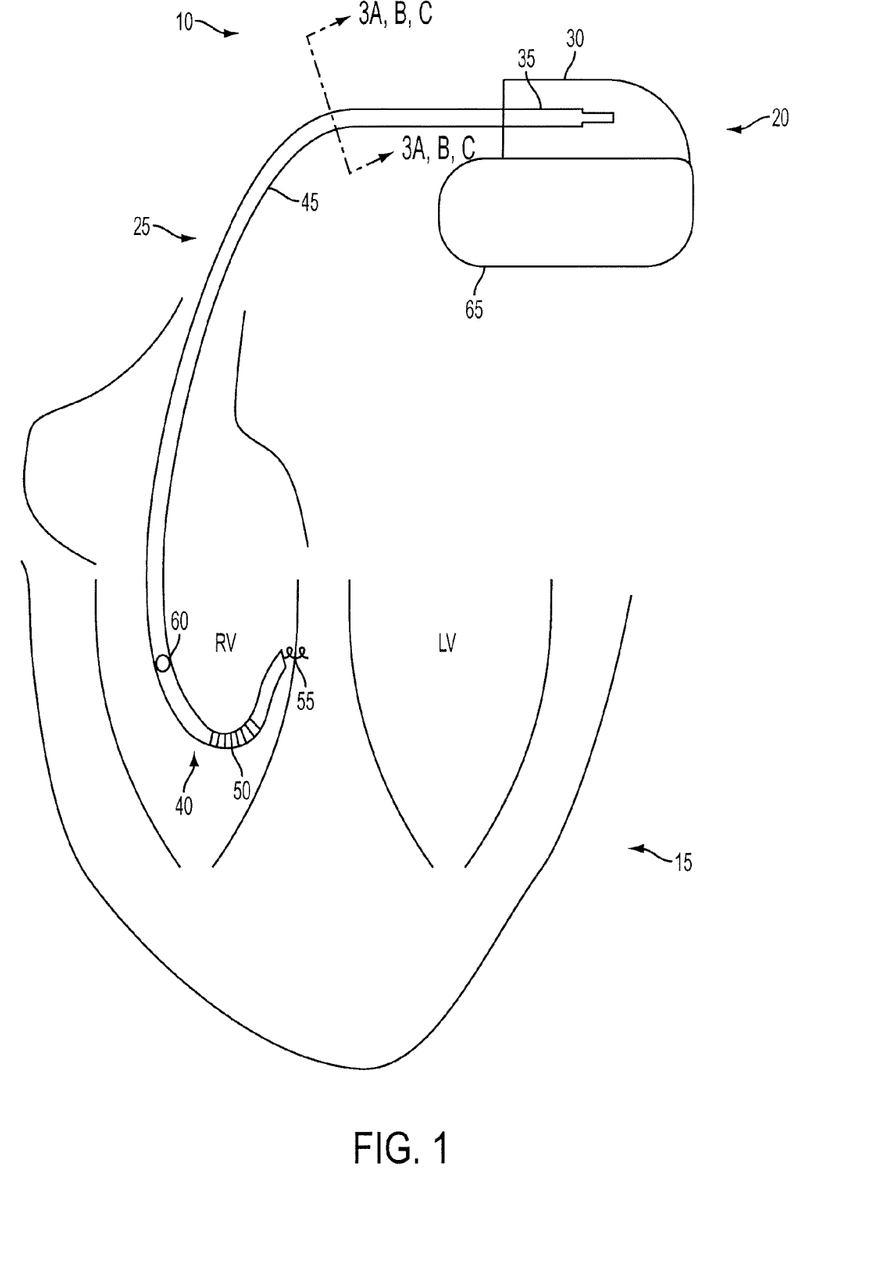
FIG. 1 is a diagram of an example implantable stimulator with a lead system whose distal portion is shown positioned within a heart.

One example of such an implantable electrical stimulation system is shown in FIG. 1. In this example, the stimulation system is an implantable cardioverter defibrillator (ICD) 10, which is shown implanted within a patient. Generally, the ICD 10 includes a pulse generator device 20 that may be implanted, for example, in a subcutaneous pectoral region of the patient. The ICD 10 also generally includes an endocardial defibrillator lead 25 that is connected, at a proximal end, to the implantable pulse generator device 20. The lead 25 has a distal portion 40 that may be positioned within a chamber of the patient's heart 15, for example, in the right ventricle (RV) as shown in FIG. 1. The distal portion 40 of the lead 25 includes, in the FIG. 1 example, a distal defibrillation coil electrode 50, as well as a pressure sensing port 60 into a lumen of the PTC (not shown in FIG. 1) that extends proximally within the lead 45.

The pulse generator device 20 is capable of generating appropriate stimulation pulses, including pacing, cardioverting and defibrillation pulses, that may be delivered to the heart 15 using the lead 25 and other leads that also may be used with the system but not shown in FIG. 1 for clarity. For example a high-energy defibrillation shock may be delivered between a coil electrode 50 located on the distal portion 40 of the lead 25 and a canister 65 of the pulse generator device 20, in cases where the canister 65 is configured to serve as an electrode. The ICD 10 may also sense cardiac electrical activity using the lead 25 (and electrode 50), as well as using other electrodes and additional leads not shown in FIG. 1 for clarity. Further yet, the ICD 10 is also capable of monitoring directly an inner-chamber pressure (in the FIG. 1 example, right ventricular pressure) using the PTC lumen that extends proximally through the lead 25 from the distal port 60.

The PTC lumen may be filled with a liquid substance having appropriate viscosity to transmit a pressure signal provided at the distal port 60. The distal port may be provided with a gel tip that is responsive to external pressure forces, and that prevents the liquid from escaping the PTC lumen and going into a chamber of the heart.

The lead 25 has a proximal portion 35 that is connectable to, and disconnectable from, the pulse generator device 20, specifically in a header 30 of the pulse generator device 20. In this example as is typical, the proximal portion 35 of the lead 25 is a male-type connection, and the header 30 is a female-type connection. The distal portion 40 of the lead 25 may be inserted transvenously into a heart chamber, for example, into the right ventricle (RV) as shown in FIG. 1. The distal portion 40 of the lead 25 may have an attachment mechanism 55 provided at a distal tip as shown in FIG. 1, so as to secure the distal tip of the lead 25 to tissue, for example, tissue of the cardiac septum as shown in FIG. 1.

The lead 25 includes a lead body 45 that extends the entire length of the lead 25 and surrounds contents of the lead 25. One or more electrical signal conduits (not shown in FIG. 1) extend within the lead body 45 from the lead body's distal portion 40 (where an electrical signal conduit may be connected, for example, to the defibrillation coil electrode 50) to the lead body's proximal portion 35. In addition, the PTC is also contained within the lead body 45, and extends proximally from the lead body's distal portion 40 and specifically from the distal port 60. The PTC extends within the lead body 45 to the proximal portion 35 of the lead 25 and to a pressure transducer (not shown in FIG. 1), which may either be incorporated into the proximal portion 35 of lead 25, or within the pulse generator device 20.

Figure 2:
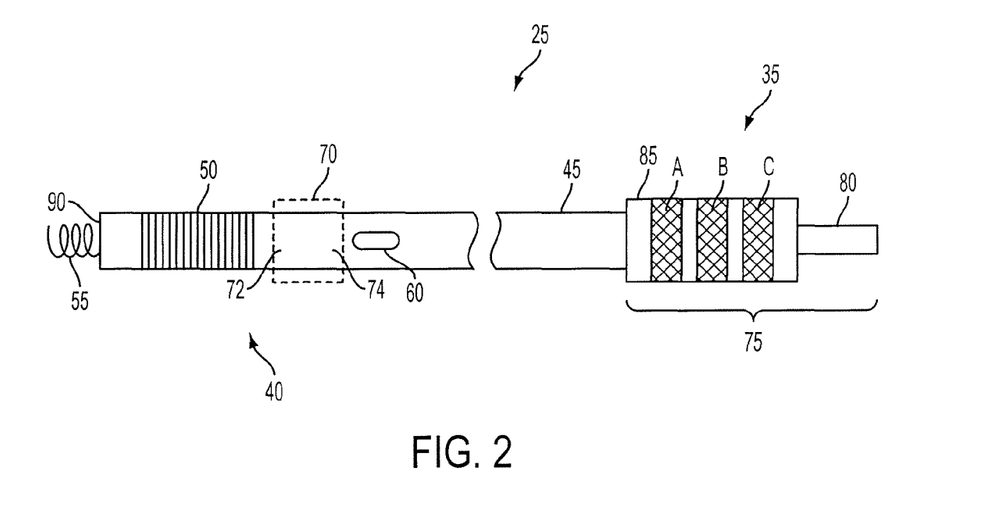
FIG. 2 is a partial diagram of a lead of the implantable stimulator shown in FIG. 1, in which a pressure transducer is located within a proximal connector of the lead.

FIG. 2 shows an embodiment of the lead 25 shown in FIG. 1, in more detail. In this embodiment, a pressure transducer is housed within the proximal portion 35 of the lead 25. The lead 25 in this example has a standard IS-4 connector 75 located at the proximal portion 35 of the lead 25. The IS-4 connector 75 that has an enlarged diameter lead body portion 85 on which is formed three separate electrical contacts, namely, contacts A, B, and C. Each of these contacts extends around an outer circumference of the connector 75. The contacts are positioned so as to contact corresponding contacts provided in a female connector on the pulse generator device header 30 (FIG. 1), when the lead 25 is plugged in to the pulse generator device 20. In some implementations, two of the contacts (for example, B and C) may be used for providing an electrical pressure signal output from a pressure sensor transducer (not shown in FIG. 1) contained inside the connector 75, whereas the third contact (A) may be used for providing a connection to the defibrillator coil electrode 50.

Various connection configurations may be used in different implementations. For example, in the case of bi-polar leads with multiple electrodes at a distal end, two of the contacts may be used for making connections to electrodes, and there may be a need to multiplex so as to use one or more contacts for both transduced pressure signals and signals coming from or to the electrodes. In addition, different standard contact configurations may be used, such as IS-1 and DF-4, as just a couple examples.

Additionally, the lead 25 has a guidewire lumen entry port 80 that extends proximally from a proximal end of the enlarged lead body portion 85. The guidewire lumen entry port 80 is provided to facilitate implantation and positioning of the lead 25, and specifically its distal portion 40, in a heart chamber using a guidewire or stylet (not shown in FIG. 2) that is inserted into the proximal end of the guidewire lumen entry port 80. The lead 25 would also have a guidewire lumen (not shown in FIG. 1) that extends distally from the entry port 80, within the lead body 45, and out of a port located at a distal end 90 of the lead 25.

FIG. 2 also illustrates that the lead 25 may optionally (or alternative to the PCT lumen entry port 60) have a bladder device 70, or sheath, which is located at the distal portion 40 of the lead 25 and is a part of the pressure sensing components of the lead 25. Such a bladder device 70 encompasses a portion of the lead body 45, including an entry port to a PTC lumen that would be underneath the bladder device 70 (that entry port not being shown in FIG. 2). Distal and proximal circumferential regions 72 and 74 of the bladder device 70 may be sealed to the lead body 45, thereby forming a chamber between the bladder device 70 and the lead body 45 between the seals of the circumferential regions 72 and 74. A fluid may be contained in this chamber, and would be in fluid communication with fluid in the PTC lumen extending proximally within the lead body 45 from the lumen entry port under the bladder device 70. Accordingly, with the use of the bladder device 70, pressure forces acting on an entire outer surface of the bladder device 70, all around its circumference, will provide a pressure input on the entry port to the PTC lumen under the bladder device 70.

Figure 3A:
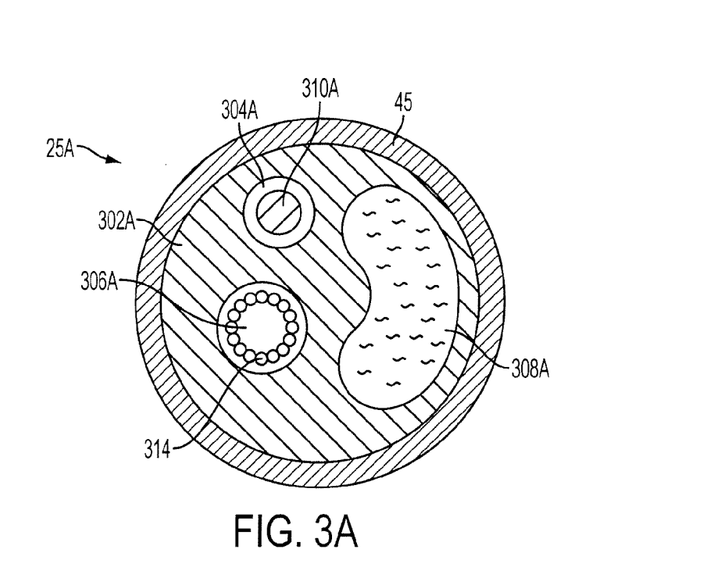
FIGS. 3A-3C are lateral cross-sectional diagrams of three different implementations of the lead shown in FIG. 2.
Figure 3B:
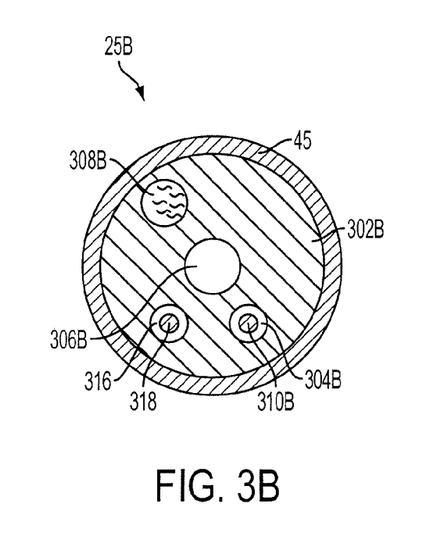
Figure 3C:
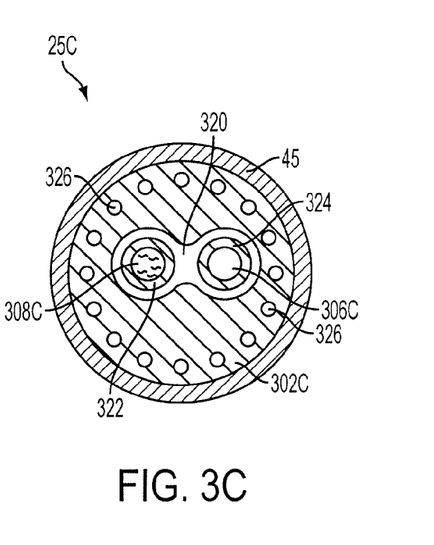

Three alternative implementations of the lead 25 shown in FIGS. 1 and 2 are shown by lateral cross section in FIGS. 3A, 3B, and 3C. In FIG. 3A, an outer jacket of the lead 25A serves as the lead body 45, and may be made of silicone or urethane material, for example. The outer jacket 25A provides a protective coating for a lead internal support structure 302A contained within the outer jacket 25A. The internal support structure 302A in the FIG. 3A embodiment has formed therein three lumens, specifically a cable conductor lumen 304A, a guidewire (or stylet) lumen 306A, and a PTC lumen 308A.

Within the cable conductor lumen 304A is a defibrillator cable conductor 310A, which is connected at a distal end to the coil electrode 50 shown in FIGS. 1 and 2. As discussed previously, the guidewire lumen 306A provides a lumen within which a guidewire or stylet would be inserted for positioning of the lead 25A, and therefore, a guidewire or stylet may be advanced into the guidewire lumen entry port 80 (FIG. 2) and advanced distally to the lead distal end 90. The guidewire lumen 306A may also have contained therein an optional coil conductor 314. Other conductors could be used for structures used in connection with the fixation member 55 (FIGS. 1 and 2), for example, for attaching the lead to the heart wall. A conductor extending through the lead 25 may also be used for heart stimulation in the form of pacing, for example. Alternatively or additionally, a conductor passing through a lumen may be attached to a sensing electrode, such as a ring electrode.

The PTC lumen 308A in the FIG. 3A example has a somewhat elongated and curved cross-section, generally in a shape of a peanut shell, so as to make efficient use of the cross-sectional area of the lead 25A and therefore minimize the overall diameter of the lead 25A. The PTC lumen 308A is filled with a pressure-transmitting substance such as a liquid. Suitable substances filled in the PTC lumen 308A include liquid perfluorocarbon, silicone or fluorosilicone oils, and saline, to name a few examples.

Turning now to the lead 25B shown in FIG. 3B, the lead internal support structure 302B in this implementation has formed therein four lumens. Specifically, the four lumens are a circular guidewire lumen 306B formed in a cross-sectional center of the lead internal support structure 302B, a circular liquid-filled PCT lumen 308B, and two cable conductor lumens 304B and 316 (instead of one such lumen as is the case in the FIG. 3A implementation).

The first cable conductor lumen 304B contains a defibrillator cable conductor 310B, which is connected at a distal end to the coil electrode 50 shown in FIGS. 1 and 2. The second cable conductor lumen 316 contains an additional cable conductor 318, which may be connected to another electrode provided at a distal portion of the lead 25B. The additional electrode supported by the FIG. 3B lead 25B may be used, for example, for sensing.

In the next implementation of the lead 25C shown in FIG. 3C, the internal lead support structure 302C has formed in a central region a joint PTC/guidewire tube lumen 320. This central lumen 320 has contained therein both a guidewire tube 324 in which is formed a guidewire lumen 306C, and a PTC 322 in which is formed a PTC lumen 308C. In addition, coaxial coils 326 are embedded within an outer peripheral region of the lead internal support structure 302C. The coaxial coils 326 provide electrical connection to the defibrillation coil electrode 50 shown in FIGS. 1 and 2.

Figure 4:
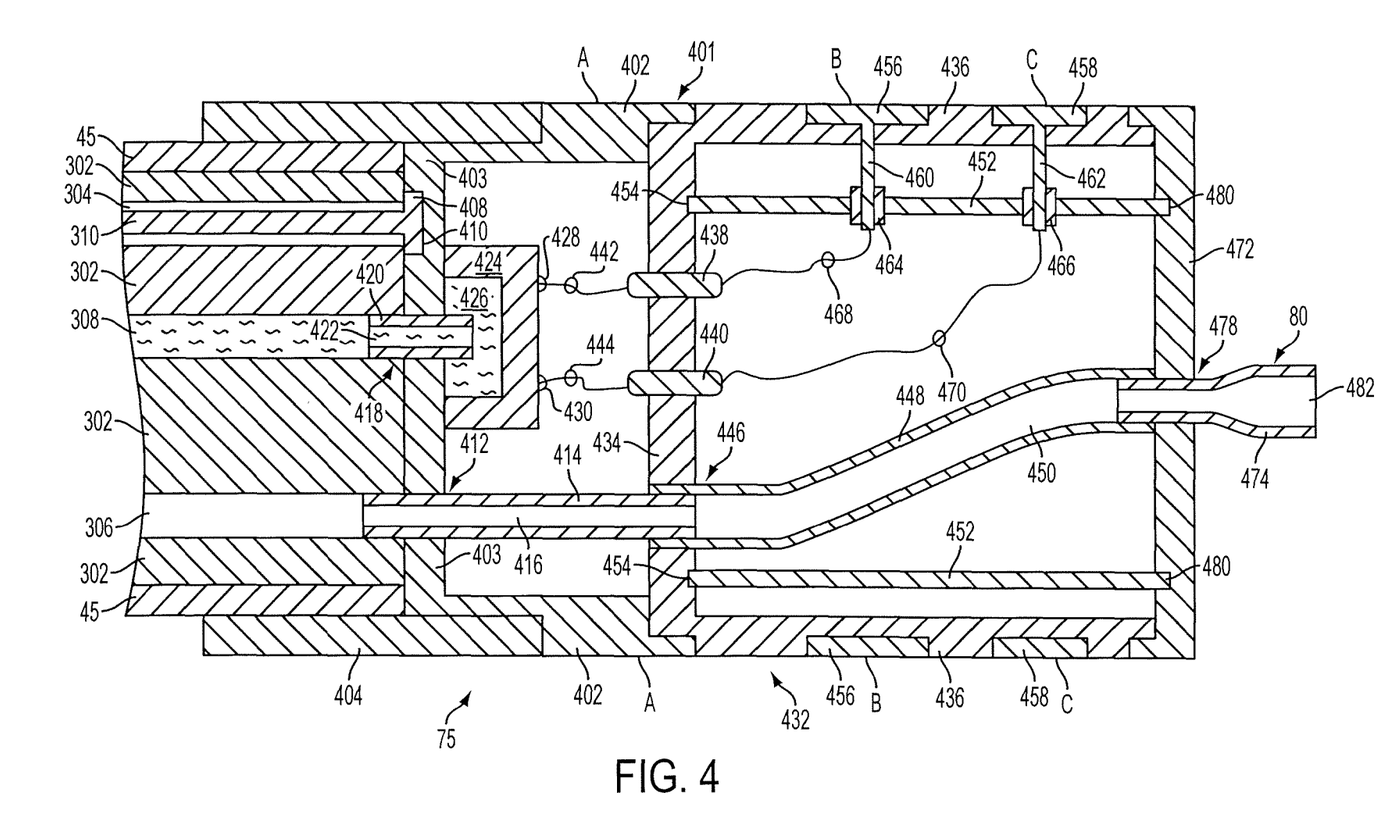
FIG. 4 is a longitudinal cross-sectional diagram of a proximal portion of an implementation of the lead shown in FIG. 2.

Turning now to FIG. 4, there is shown a cross-section of an embodiment of the proximal portion 35 of the lead 25 shown in FIG. 2, including the connector 75 and a proximal portion of the lead body 45 and its internal structure. The cross-section shown in FIG. 4 is a longitudinal cross-section through a longitudinal center of the lead proximal portion 35.

The lead body 45 and lead internal support structure 302 are shown on a left-hand side of FIG. 2. The lead internal support structure 302 includes three lumens, a longitudinally centered, liquid-filled PTC lumen 308, a defibrillator electrode conductor lumen 304 that is offset from center, and a guide-wire lumen 306 that is also offset from center. A defibrillator cable conductor 310 is shown within the cable conductor lumen 304, and has on its proximal end a connector portion 408 that is connected to, and within a recess of, a conductive cup member 401 that also serves as contact A. Thus, the defibrillator cable conductor 310 (and coil electrode 50 shown in FIG. 2) connects to the pulse generator device 20 (FIG. 1) via the electrical contact A.

The conductive cup member 401 comprises a circular-shaped bottom portion 403 and tubular side portions 402 that are connected at a peripheral region of the circular-shaped bottom portion 403. A bottom surface of the conductive cup member 401 (that is, a bottom of the cup member 401) abuts against a distal end of the lead body 45 and its internal support structure 302. A tubular sheath 404 surrounds a proximal portion of the lead body 45 and a distal portion of the cup member tubular side portion 402, and is affixed to outer surfaces of each to hold a bottom surface of the bottom portion 403 of the cup member 401 against, and in proper alignment with, a distal end of the lead body 45 and its internal support structure 302.

The bottom portion 403 of the cup member 401 contains two holes: a guide-wire lumen hole 412 and a PCT lumen hole 418. The guide-wire lumen hole 412 is aligned end-to-end with the guide-wire lumen 306 formed in the lead internal support structure 302 within the lead body 45. Inserted in the guide-wire lumen hole is a first guide-wire lumen connecting tube 414. The first guide-wire lumen connecting tube 414 has a lumen 416 extending through it, which lumen 416 is in communication with the guidewire lumen 306 formed in the internal support structure 302. The first connecting tube 414 extends for a short distance distally from the cup member bottom portion 403, and into the guide-wire lumen 306 formed in the internal support structure 302. This distal extension is to maintain alignment of the guide-wire lumen through the bottom portion 403 of the cup member 401. The first guide-wire lumen connecting tube 414 also extends for a distance proximally from the cup member bottom portion 403.

The PTC lumen hole 418 is aligned end-to-end with the PTC lumen 308 formed in the lead internal support structure 302 within the lead body 45. The PTC lumen hole 418 also has inserted into it a connecting tube 420, which will be referred to as a PTC lumen connecting tube. The PTC connecting tube 420 has a lumen 422 extending through it, which lumen 422 is in communication with the PTC lumen 308 formed in the internal support structure 302. The PTC connecting tube 420 extends for a short distance distally from the cup member bottom portion 403, and into the PTC lumen 308 formed in the internal support structure 302. This distal extension is to maintain alignment and hermetic seal of the PTC lumen through the bottom portion 403 of the cup member 401, so that a liquid that fills the lumen does not seep into a crack between the lead internal support member 302 and the bottom portion 403 of the cup member 401. The PTC connecting tube 420 also extends for a distance proximally from the cup member bottom portion 403 and into a fluid chamber 426 of a pressure sensor transducer 424.

The pressure sensor transducer 424 is positioned within the conductive cup member 401, against the bottom portion 403 of the cup member 401 adjacent the PTC lumen hole 418. The sensor transducer 424 has a cup shape, a periphery of which is affixed to the bottom portion 403 of the cup member 401, thus forming the fluid chamber 426. The sensor transducer 424 is adapted to sense a pressure of the fluid within chamber 426, for example, by a pressure sensing surface adjacent the fluid chamber 426, which produces an electrical output at contacts 428 and 430 indicative of a pressure level of the fluid within the fluid chamber 426. Thus, pressure variations that occur at the distal port 60 (FIG. 2) for the pressure transmission lumen 308 (FIG. 4) are transmitted within the PTC lumen 308, through the PTC connecting tube 420, and into the fluid chamber 426 where fluid pressure is sensed by the sensor transducer 424.

A second cup member 432 connects to the first cup member 401. The second cup member 432 is non-conductive, and has a circular-shaped bottom portion 434 and a tubular side portion 436. A periphery of the non-conductive cup member bottom portion 434 is shaped to mate with a complementary shape formed in a periphery of a proximal end of the first cup tubular side portion 402. As such, the periphery of the non-conductive cup member bottom portion 434 may, as shown, be affixed to the proximal end periphery of the conductive cup member side portion 402.

The non-conductive cup member 432 has a guide-wire lumen hole 446 extending through it. A second guide-wire lumen connecting tube 448 is positioned to extend through the hole 446, and extend proximally from the hole. The hole 446 is positioned in the non-conductive cup member bottom portion 434 so that the first guide-wire lumen connecting tube 414 may be placed, upon assembly and as shown in FIG. 4, into the hole 446, and more particularly, within a lumen 450 of the second guide-wire lumen connecting tube 448 extending through the hole 446. An outer surface of the second guide-wire lumen connecting tube 448 may be affixed to an inner surface of the second cup member bottom portion 434, at the hole 446, and an outer surface of the first guide-wire lumen connecting tube 414 may be affixed to an inner surface of the second guide-wire lumen connecting tube 448.

Two separate electrical contacts 438 and 440 are formed in two separate through-holes formed in the non-conductive cup member bottom portion 434. At a distal side of the non-conductive cup member bottom portion 434, two wires 442 and 444 connect the contacts 438 and 440 to the pressure sensor transducer electrical contacts 428 and 430.

A circular recess 454 is formed in a peripheral region of the non-conductive cup member bottom portion 434, on a distal surface of the bottom portion 434. An inner tube 452 is positioned within the second, non-conductive cup member 432, coaxial with, and spaced from, the tubular side portion 436 of the cup member 432. A distal end of the inner tube member fits into the circular recess 454. A circular-shaped cap member 472 is affixed to a proximal end of the non-conductive cup member 432 tubular side portion 436. A peripheral region of the cap member 472 is configured to mate with, and be affixed to as shown in FIG. 4, a complementary surface formed in the proximal portion of the non-conductive cup member side portion 436. A circular recess 480, similar to circular recess 454, is formed in a peripheral region of the cap member 472, on a distal surface of the cap member 472. When the cap member 472 is affixed to the non-conductive cup member 432, the inner tube 452 is held within the circular recesses 454 and 480.

The cap member has a centrally placed guide-wire lumen hole 478. A tubular member 474 constituting a third guide-wire lumen connecting member, having a lumen 482, extends through the guide-wire lumen hole 478. The third guide-wire lumen connecting tube 474 extends proximally from the cap member 472 a short distance, and also distally from the cap member 472. The portion of the third guide-wire lumen connecting tube 474 that extends proximally forms the guide-wire lumen entry port 80, and may be flared as shown in FIG. 4 to facilitate inserting a guide-wire or stylet into the lumen 482 of the entry port 80.

The second guide-wire lumen connecting tube 448 is connected to the third guide-wire lumen connecting tube 474. In particular, an inner surface of a proximal portion of the second guide-wire lumen connecting tube 448 fits over, and is affixed to, an outer surface of the portion of the third guide-wire lumen connecting tube 474 that extends distally from the cap member 472. As such, the third connecting tube lumen 482 is in communication with the second connecting tube lumen 450, and thus the guide-wire lumen extends all the way from the entry port 80 to an opening at the distal end 90 of the lead 25 (FIG. 2).

Two separate circumferential bands 456 and 458 extend around an outer surface of the non-conductive cup member tubular side portion 436. The bands 456 and 458 are positioned within two circumferential recesses formed on an outer surface of the tubular side portion 436. The circumferential bands 456 and 458 form contacts B and C of the IS-4 connector 75. The bands 456 and 458 are made of a conductive material. Each of the conductive bands 456 and 458 has a contact stem 460 and 462 that extends from an inner surface of the band, and is positioned through side holes in the non-conductive cup member tubular side portion 436 and through aligned side holes in the inner tube 452. Insulators 464 and 466 may be used and placed with the holes through the inner tube 452, so as to provide electrical insulation between the conductive stems 460 and 462 in the event, for example, the inner tube 452 is made of a conductive material.

Connecting wires 468 and 470 provide electrical connection between contacts 438 and 440. As such, an electrical output from the pressure transducer sensor 424 is provided in this embodiment at contacts B and C. Accordingly, a sensor transducer 424 for a fluid-filled pressure transmission catheter type pressure sensor is provided in this embodiment shown in FIG. 4 within the proximal portion 35 of the lead 25 itself.

Figure 5A:
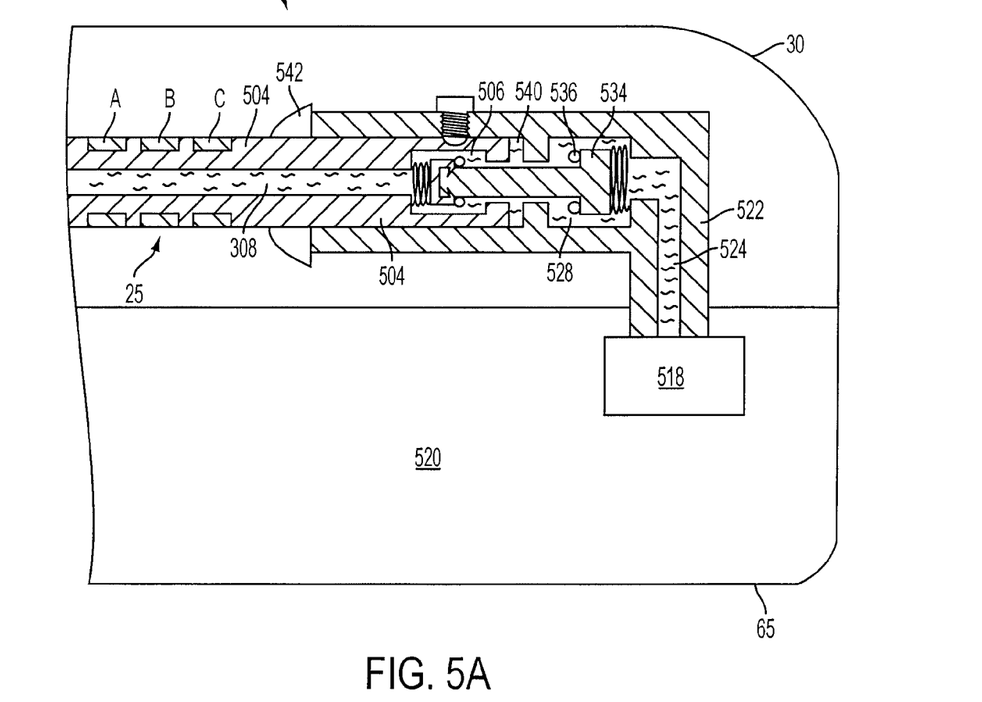
FIGS. 5A-5C are cross-sectional diagrams of a lead system in which a pressure transducer is located with a pulse generator housing.
Figure 5B:
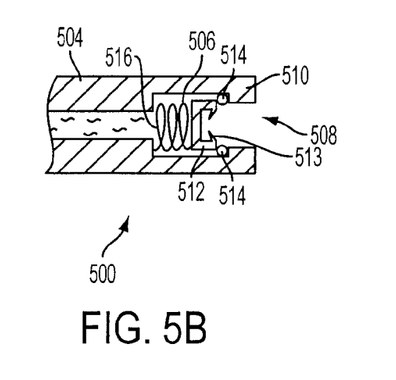
Figure 5C:
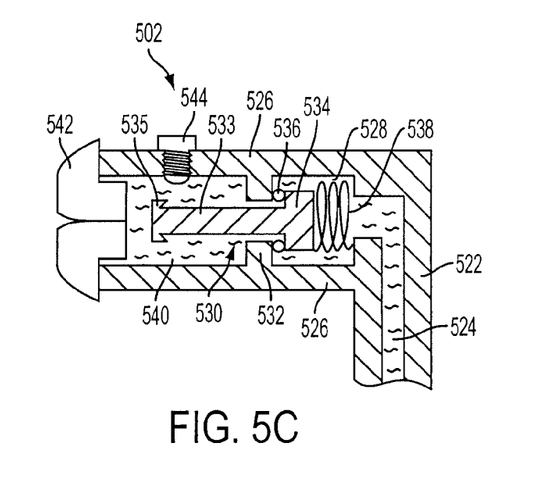

Turning now to FIGS. 5A-5C, an implementation of lead system for an implantable stimulator is shown in which a pressure transducer for a liquid-filled catheter type pressure sensing system is housed not in the lead itself as in the FIG. 4 embodiment, but rather in the pulse generator canister 65, and specifically within the header 20 of the canister 65. FIG. 5A shows a proximal portion of a lead 25 that includes a proximal lead tip 500 inserted into a lead tip receiver 502 contained within the header 30 of the pulse generator 20. FIGS. 5B and 5C show the lead tip 500 and the lead tip receiver 502 before being connected.

As shown in FIG. 5A, the PTC lumen 308 extends within a lead connector body 504. Pressure forces received at the distal pressure sensing port 60 are transmitted proximally through the lead 25, including the proximal lead connector body 504, and past the three connector contacts A, B and C. In this embodiment, the connector contacts A, B and C are not needed for the pressure sensor. Therefore, the contacts A, B and C may be used for providing electrical contacts one or more distal electrodes.

The lead tip 500, as shown in FIG. 5B, has a chamber 506 formed therein that, in this implementation, has a larger diameter than the PTC lumen 308. At a proximal end of the chamber 506 is a proximal opening 508 formed by a proximal end portion 510 of the lead connector body 504 extends inward, such that the diameter of the proximal opening 510 is smaller than an inner diameter of the chamber 506. A piston head 512 or disc is positioned within the chamber 506, and is sized to enable proximal and distal movement of the piston head 512 within chamber 506. An optional connection mechanism 513 is shown provided on a proximal side of the piston head 512, for attachment to a complementary piece as will be described later. As will be appreciated from discussion below, the connection mechanism 513 may not be needed or desired in some implementations.

An O-ring seal 514 may be affixed to a proximal surface of the piston head 512, at a peripheral region of the piston head proximal surface, as shown in FIG. 5B. The O-ring seal 514 is circular shaped, and has a diameter that is larger than the diameter of the distal opening 508. For clarification, the O-ring seal diameter actually has two diameters—an overall diameter of the circular-shape of the O-ring, and a smaller diameter of a cross-section "O" of the O-ring It is the former of these two diameters that we state to be larger than the diameter of the distal opening 508. A spring 516 is positioned distal of the piston head 512 and biases the piston head 512 proximally so that the O-ring seal 514 attached to the proximal surface of the piston head 512 is pressed against an inner distal surface of the proximal end portion 510 that surrounds the distal opening 508. Accordingly, liquid or other pressure transmitting substance is prevented from escaping from within the lead 25 prior to connection of the lead 25 to the pulse generator 20.

On the pulse generator 20 end of the system, a pressure transducer 518 is contained within a main body 520 of the pulse generator 20. A receiver PTC catheter 522 having a lumen 524 formed therein is in communication with the pressure transducer 518 and extends from the main body 520 and into the header 30 of the pulse generator 20. There, the receiver PTC 522 takes a right angle so that the lumen is directed in a direction toward a female connector opening of the header 30. The PTC 522 is integrally formed with a lead tip receiver body 526.

The lead tip receiver body 526, as shown in FIG. 5C, has a chamber 528 formed therein that, in this implementation, has a larger diameter than the receiver PTC lumen 524. At a distal end of the chamber 528 is an opening 530 formed by an inner wall portion 532 of the lead tip receiver body 526 that extends inwardly, such that the diameter of the opening 530 is smaller than an inner diameter of the chamber 528. A piston head 534 or disc is positioned within the chamber 528, and is sized to enable proximal and distal movement of the piston head 534 within the chamber 528. The piston head 534 has a stem 533 that extends distally from a distal surface of the piston head 534 and through the hole 530. An optional connection mechanism 535 is shown provided on a distal end of the stem 533, and is complementary to, for attachment with, the attachment mechanism 513 on the proximal side of the piston head 512. Again, the connection mechanisms 533 and 513 may not be needed or desired in some implementations.

An optional O-ring seal 536 is affixed to a distal surface of the piston head 534, at a peripheral region of the piston head distal surface. The O-ring seal 536 is circular shaped, and has a diameter that is larger than the diameter of the opening 530. A spring 538 may be positioned proximal of the piston head 534 and biases the piston head 534 distally so that the O-ring seal 536 attached to the distal surface of the piston head 534 is pressed against an inner proximal surface of the inner wall portion 532 that surrounds the opening 530. Again, for clarification, the O-ring seal diameter actually has two diameters—an overall diameter of the circular-shape of the O-ring, and a smaller diameter of a cross-section "O" of the O-ring It is the former of these two diameters that we state to be larger than the diameter of the opening 530.

The lead tip receiver body 526 also forms, distal of the opening 530 from the piston chamber 528, a receiving chamber 540 for the lead connector body 504. The receiving chamber has an inner diameter that is large enough to accommodate the lead connector body 504 being received within it. The lead tip receiver body 526 has a silicone septum 542 attached to its distal end. The silicone septum prevents liquid from escaping the chamber 540, but allows the lead tip receiver 500 to be inserted through the septum 542 and into the chamber 540. The septum 542 also forms a seal around the lead tip receiver 500, and specifically around the lead connector body 504. A set screw 544 is provided that extends through a screw hole provided through the lead tip receiver body 526 adjacent to the receiving chamber 540, such that when the lead tip body 504 is positioned within the receiving chamber 540, the set screw 544 may be tightened to secure the lead tip body 504 within the receiving chamber 540.

When the lead tip 500 is plugged in to the lead tip receiver 502, a proximal end of the lead tip 500 penetrates the septum 542, such that the lead tip receiver body 504 may be positioned within the receiving chamber 540. In some implementations pressure generated with the initial insertion at the septum 542 may flush any air proximal of the piston head 512 that may be trapped. In other implementations, a air bleeding mechanism may be added to bleed any trapped air from within the pressure-transmitting liquid chambers. Advancing the lead tip body 504 into the receiving chamber 540 causes the stem 533 attached to piston head 534 to come into contact with the piston head 512.

Further advancement of the lead tip body 504 into the receiving chamber 540 causes, in some implementations, the complementary connection mechanisms 512 and 535 to become connected, as shown in FIG. 2A. In particular, a forward distal end of the stem 533 causes a forward surface of piston head 512 to urge apart, and after a larger diameter portion of stem 533 extends beyond a catch in the piston head 512, the piston 512 may snap back to retain the connection mechanism of the stem 533. Thereafter, the piston head 534 and stem 533 will be connected to piston head 512, and move proximally and distally with the other in accordance with pressure changes. The connection mechanisms 512 and 535 may be constructed so that they will release from one another without breaking, in a presence of sufficient force being applied during removal of the lead 25 from the pulse generator header 30. In addition, such a connection may not be needed or desirable in some implementations where coordinated movement of the piston heads 512 and 534 may not be necessary.

Eventually, when the lead tip body 504 is in proper position within the receiving chamber 540, the spring forces provided by springs 516 and 538 will have been overcome, and the seal provided by the O-ring seals 514 and 536 will no longer be provided. As such, the lead PTC lumen 308, chamber 506, a remaining portion of the chamber 540 not occupied by lead tip body 504, chamber 528, and the receiver PTC lumen 524 are all in fluid communication, and will be filled with a pressure transmitting liquid. As such, a pressure provided at the distal PTC lumen port 60 (FIG. 1) may be transmitted through the lead 25, into the pulse generator header 30 and main body 520, where the pressure may be measured by the transducer 518 (FIG. 5A).

In a variation of the FIG. 5A-5C embodiment, pressure-transmitting liquid may not be provided in receiving chamber 540, and as such, the septum 542 may not be needed. In such an embodiment, a sealing structure may be provided between piston head 512 and lead connector body 504, so that no fluid from within the lead PTC lumen 308 would be permitted to pass proximal of the piston head 512. Similarly, a sealing structure may also be provided between piston head 534 and body 526, so that no fluid from within the receiver PTC lumen 524 would be permitted to pass distal of the piston head 534. In such a case, the connection mechanisms 513 and 535 may be required, so that the pistons 512 and 534 would translate longitudinally with one another responsive to changes in pressure. For example, a pressure within lead PTC lumen 308 may act upon piston 512, and hence piston 534, which pressure force would be transmitted through the pressure transmitting liquid contained in the receiver PTC lumen 524. In this embodiment, a potential issue of air in the chamber 540 would not be an issue, and further there would be no potential issue of liquid escaping PTC lumens during the connection process.

Figure 6:
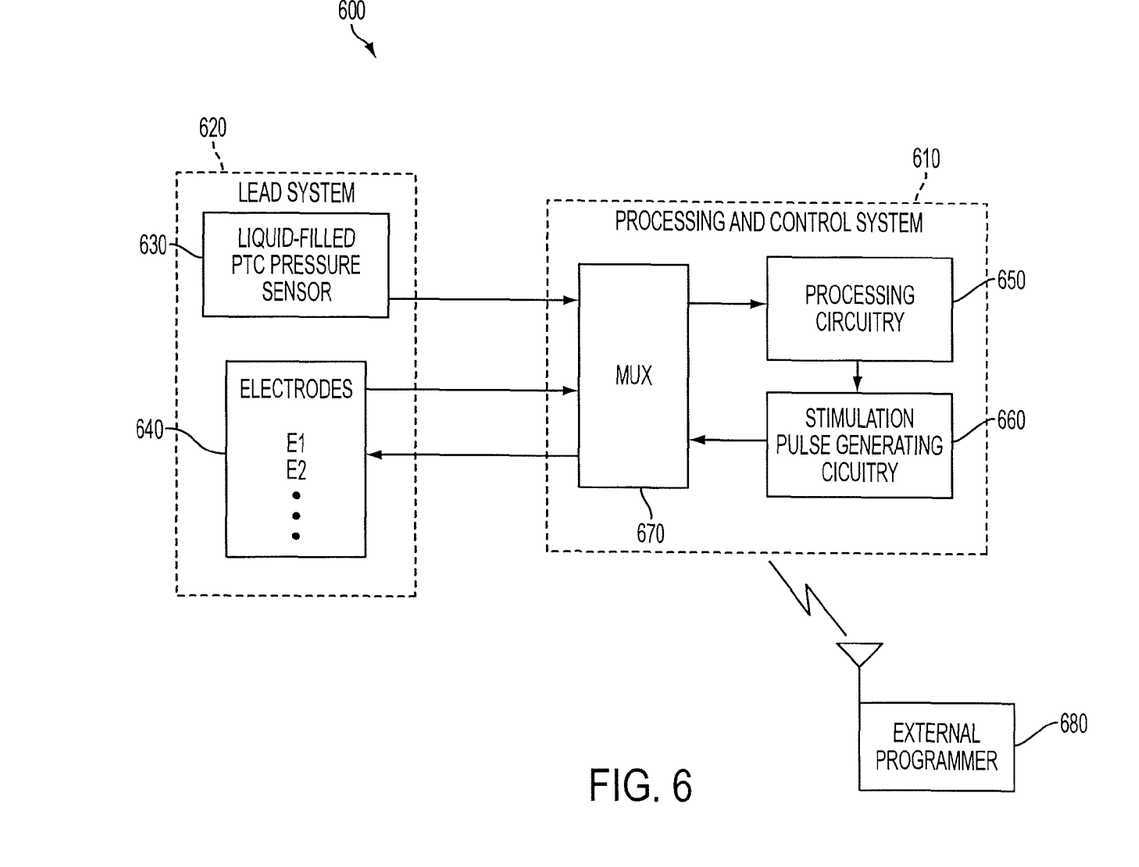
FIG. 6 is a block diagram of an implantable stimulator and external equipment.

Referring now to FIG. 6, a cardiac stimulation system 600 includes a processing and control system 610 that may be contained within a pulse generator housing, such as the housing 65 of the pulse generator 20 shown in FIG. 1. The system 600 also includes a lead system 620 that includes a liquid-filled PTC pressure sensor 630 and various electrodes 640. The lead system 620 may be made up of one or more leads that may be plugged in to a header of a pulse generator housing, for example. For example, the lead system 620 may include a ventricular lead with a distal defibrillation coil electrode and a pressure transmission catheter as described previously, as well as an additional electrode provided for example on another lead and/or an electrode integrated into the pulse generator housing.

The processing and control system 610 includes processing circuitry 650 that may process sensed signals from the pressure sensor 630 (pressure signals) or from the electrodes 640 (intracardiac electrograms, or Egrams, for example, or a subcutaneous electrocardiogram, or ECG, signal). The processing circuitry 650 may have memory in which control program instructions are stored, memory for storing various parameters that may be programmed, a processor for executing program instructions to control operation of the system, and input-output circuitry to control communications, including communications for example with external programming and communication equipment 680 via wireless telemetry.

The processing and control system 610 may also include stimulation pulse generating circuitry 660 that may operate to generate pacing, cardioverting, or defibrillation pulses that may be delivered to the electrodes 640. The stimulation and pulse generating circuitry 660 would be controlled by the processing circuitry 650. The system 610 may also include multiplexing circuitry to multiplex signals delivered to and received from the lead system 620. The circuitry provided in the processing and control circuitry 610 may be implemented in one or more application-specific integrated circuits (ASIC's), for example.

Figure 7:
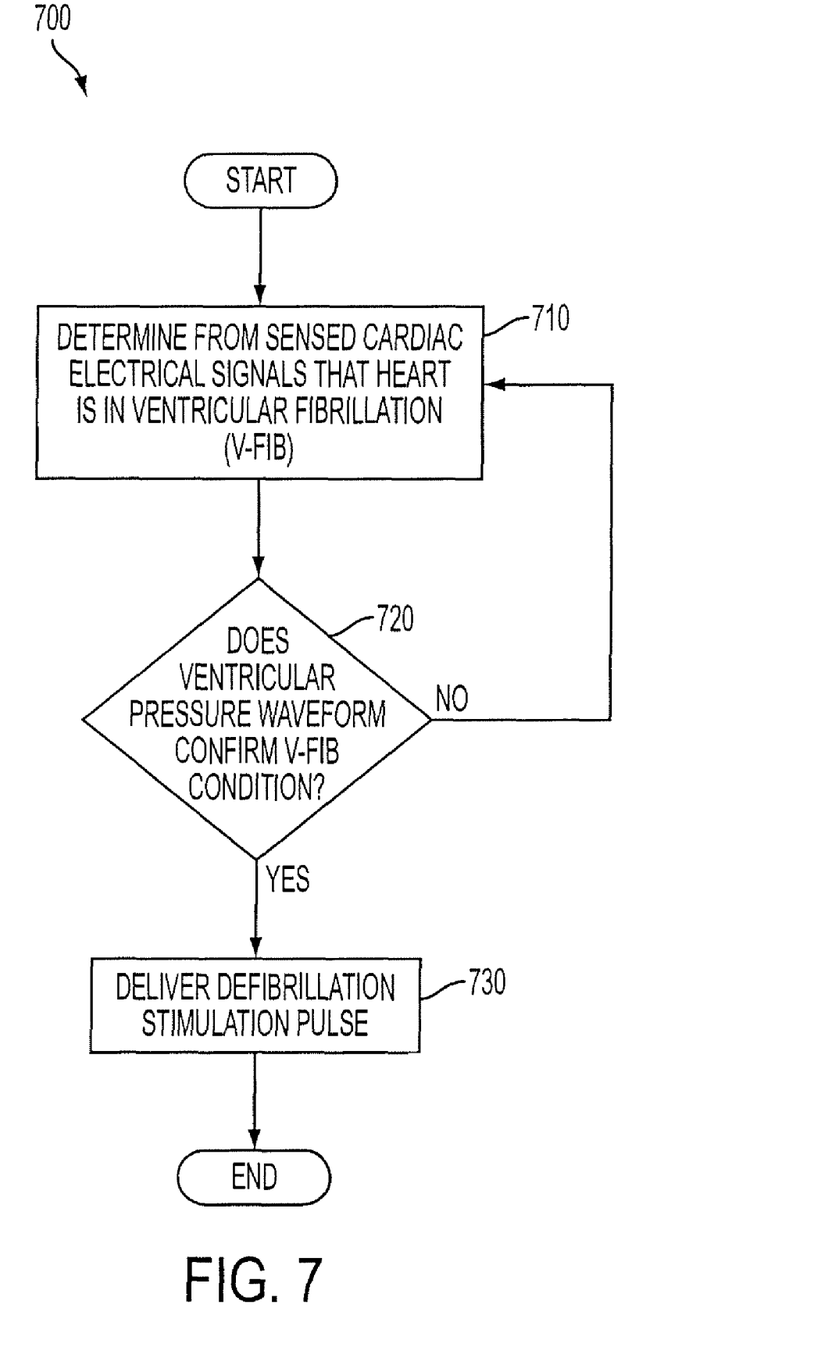
FIG. 7 is a flowchart of a method of providing defibrillation therapy with an implantable defibrillator.

Referring now to FIG. 7, a method 700 is provided that may be implemented with the lead systems described in this document. The method 700 is particularly advantageous in avoiding unnecessary and harmful defibrillation shocks being delivered by an implantable defibrillator.

The method 700 starts at step 710 in which a determination is made from sensed cardiac electrical signals that the heart is in a ventricular fibrillation (V-Fib) condition. The signals may be obtained by various electrodes, such as the electrodes 640 provided in the lead system 620 shown in FIG. 6. The sensed cardiac electrical signals may be electrogram signals obtained from an electrode positioned within a heart chamber, or a subcutaneous electrocardiogram, or ECG signal, by way of example. A variety of different algorithms may be employed to assess the cardiac electrical activity in an attempt to determine from the sensed electrical signals (and perhaps other sensors as well, including pressure signals), whether the heart is presently in a V-Fib condition.

After such a determination has been made, delivery of a defibrillation pulse is not immediately delivered. Rather, a confirmation of the V-Fib condition is first made at step 720 from pressure signals that are directly measured from within the ventricular chamber, for example. The directly measured pressure intra-chamber pressure signals may be obtained, for example, using the lead systems with liquid-filled PTC type pressure sensors as described in this document. The pressure signals may constitute a waveform over the preceding several seconds and minutes. In the event that the pressure signals confirm the V-Fib condition, a defibrillation shock may thus be delivered at step 730. As such, more assurance may be achieved that pain defibrillation shocks are not being delivered unnecessarily.

Although the lead systems described above are described primarily in the context of implantable defibrillators, it will be appreciated that the designs and techniques described in this document may be applicable to other stimulation systems that provide stimulation pulses to cardiac, nerve or other tissue.

A number of embodiments of the invention have been described. Nevertheless, it will be understood that various modifications may be made without departing from the spirit and scope of the invention. Accordingly, other embodiments are within the scope of the following claims.

What is claimed is:
1. An implantable defibrillator system comprising:
an implantable pulse generator component adapted for subcutaneous implantation in a subject; and
an endocardial lead comprising:
an elongate lead body having a distal portion adapted for implantation within a heart chamber and a proximal portion adapted to be connected to the implantable pulse generator component, the elongate lead body having a length that extends from a chamber of a subject's heart to a subcutaneous region of the subject;
an elongate electrical conductor extending, within the lead body, from the lead body distal portion and to the lead body proximal portion;

a pressure transmission catheter comprising a lumen extending, within the lead body, from a distal pressure sensing portion positioned at the lead body distal portion and to the lead body proximal portion, the pressure transmission catheter lumen being filled with a pressure transmitting substance;

wherein the implantable pulse generator component is adapted to monitor, using the pressure transmission catheter, a pressure signal present at the distal pressure sensing portion, is adapted to evaluate the monitored pressure signal, and is adapted to avoid application of an unnecessary defibrillating shock if the monitored pressure signal is pulsating in a manner that indicates an absence of a ventricular fibrillation condition.

2. The implantable defibrillator system of claim 1, wherein the endocardial lead comprises a pressure transducer positioned within the lead body proximal portion.

3. The implantable defibrillator system of claim 1, wherein the implantable pulse generator component comprises a pressure transducer.

4. The implantable defibrillator system of claim 1, wherein the pressure transmitting substance is a pressure transmitting liquid.

5. An endocardial defibrillator lead comprising:
an elongate lead body having a distal portion adapted for implantation within a heart chamber and a proximal portion adapted to be connected to an implantable pulse generator component, the elongate lead body having a length that extends from a chamber of a subject's heart to a subcutaneous region of the subject;
an elongate electrical conductor extending, within the lead body, from a defibrillation electrode positioned at the lead body distal portion and to the lead body proximal portion;
a pressure transmission catheter comprising a lumen extending, within the lead body, from a distal pressure sensing portion positioned at the lead body distal portion and to the lead body proximal portion, the pressure transmission catheter lumen being filled with a pressure transmitting substance.

6. The endocardial defibrillator lead of claim 5, further comprising a pressure transducer positioned within the lead body proximal portion.

7. The endocardial defibrillator lead of claim 5, wherein the pressure transmission catheter further comprises a piston component that moves longitudinally within the lead body in response to changes in pressure at the distal pressure sensing portion, wherein the piston is adapted for attachment to, and for movement with, a component within the implantable pulse generator, so that pressure transmitted through the substance within the pressure transmission catheter lumen is detectable within the implantable pulse generator component.

8. The endocardial defibrillator lead of claim 5, wherein a proximal lead tip of the lead is configured to mate with a lead tip receiver formed within an implantable pulse generator, and upon connection form a non-interrupted path of pressure transmitting substance that extends from the lead pressure transmission catheter lumen to a receiver pressure transmission catheter lumen provided in the implantable pulse generator.

9. The endocardial defibrillator lead of claim 5, wherein the pressure transmitting substance is a pressure transmitting liquid.

* * * * *